United States Patent [19]

Gelfand et al.

[11] Patent Number: 5,210,015
[45] Date of Patent: May 11, 1993

[54] HOMOGENEOUS ASSAY SYSTEM USING THE NUCLEASE ACTIVITY OF A NUCLEIC ACID POLYMERASE

[75] Inventors: David H. Gelfand; Pamela M. Holland, both of Oakland; Randall K. Saiki, Richmond; Robert M. Watson, Berkeley, all of Calif.

[73] Assignee: Hoffman-La Roche Inc., Nutley, N.J.

[21] Appl. No.: 563,758

[22] Filed: Aug. 6, 1990

[51] Int. Cl.$^5$ .................. C12Q 1/68; C07H 21/00
[52] U.S. Cl. ........................................ 435/6; 435/18; 435/91; 435/196; 435/805; 436/501; 436/63; 436/815; 536/24.3; 935/17; 935/77; 935/78; 935/88
[58] Field of Search .............. 435/6, 18, 91, 196, 435/805; 436/501, 63, 815; 536/27; 935/17, 77, 78, 88

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |
| 4,914,210 | 4/1990 | Levenson et al. | 548/413 |
| 5,011,769 | 4/1991 | Duck et al. | 435/6 |
| 5,108,892 | 5/1992 | Burke et al. | 435/6 |

FOREIGN PATENT DOCUMENTS 357011  3/1990  European Pat. Off. .
8909284 10/1989  PCT Int'l Appl. .
8910979 11/1989  PCT Int'l Appl. .

OTHER PUBLICATIONS

Lawyer et al., (1989) J. Biol. Chem. 264:6427–6437.
Gelfand, "Taq DNA Polymerase" in PCR Technology, Erlich, ed., Stockton Press 1989.
Settow et al. (1972) Journal of Biological Chemistry, vol. 247, No. 1, pp. 224–231.
Lehman et al. (1973) Journal of Biological Chemistry, vol. 248, No. 22, pp. 7717–7723.

*Primary Examiner*—Margaret Moskowitz
*Assistant Examiner*—Ardin H. Marschel
*Attorney, Agent, or Firm*—George M. Gould; Dennis P. Tramaloni; Stacev R. Sias

[57] ABSTRACT

The present invention is directed to a process of detecting a target nucleic acid using labeled oligonucleotides. This process uses the 5' to 3' nuclease activity of a nucleic acid polymerase to cleave annealed labeled oligonucleotide from hybridized duplexes and release labeled oligonucleotide fragments for detection. This process is easily incorporated into a PCR amplification assay.

38 Claims, 10 Drawing Sheets

LANE  1 2 3 4 5 6 7 8 9 10 11 12

LANE  1 2 3 4 5 6 7 8 9 10 11 12

HOMOGENEOUS ASSAY SYSTEM USING THE NUCLEASE ACTIVITY OF A NUCLEIC ACID POLYMERASE

TECHNICAL FIELD

This invention relates generally to the field of nucleic acid chemistry. More specifically, it relates to the use of the 5' to 3' nuclease activity of a nucleic acid polymerase to degrade a labeled oligonucleotide in a hybridized duplex composed of the labeled oligonucleotide and a target oligonucleotide sequence and form detectable labeled fragments.

BACKGROUND OF THE INVENTION

Investigational microbiological techniques are routinely being applied to diagnostic assays. For example, Falkow et al., U.S. Pat. No. 4,358,535 disclose a method for detecting pathogens by spotting a sample e.g., blood, cells, saliva, etc. on a filter (e.g., nitrocellulose), lysing the cells, and fixing the DNA through chemical denaturation and heating. Then, labeled DNA probes are added and allowed to hybridize with the fixed sample DNA, hybridization indicating the presence of the pathogen's DNA. The sample DNA in this case may be amplified by culturing the cells or organisms in place on the filter.

A significant improvement in DNA amplification, the polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing, and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., (1985) *Science* 230:1350.

Detection methods generally employed in standard PCR techniques use a labeled probe with the amplified DNA in a hybridization assay. For example, commonly-owned copending patent application U.S. Ser. Nos. 899,344 and 178,276 to Erlich et al., disclose assay methods wherein the PCR-amplified DNA is first fixed to a filter and then a specific oligonucleotide probe is added and allowed to hybridize. Preferably, the probe is labeled, e.g., with $^{32}P$, biotin, horseradish peroxidase (HRP), etc., to allow for detection of hybridization. The reverse is also suggested, that is, the probe is instead bound to the membrane and the PCR amplified sample DNA is added.

Other means of detection include the use of fragment length polymorphism (PCR FLP), hybridization to allele-specific oligonucleotide (ASO) probes (Saiki et al., (1986) Nature 324:163), or direct sequencing via the dideoxy method (using amplified DNA rather than cloned DNA). The standard PCR technique operates (essentially) by replicating a DNA sequence positioned between two primers, providing as the major product of the reaction a DNA sequence of discrete length terminating with the primer at the 5' end of each strand. Thus, insertions and deletions between the primers result in product sequences of different lengths, which can be detected by sizing the product in PCR-FLP. In an example of ASO hybridization, the amplified DNA is fixed to a nylon filter (by, for example, UV irradiation) in a series of "dot blots", then allowed to hybridize with an oligonucleotide probe labeled with HRP under stringent conditions. After washing, tetramethylbenzidine (TMB) and hydrogen peroxide are added: HRP oxidizes the hydrogen peroxide which in turn oxidizes the TMB to a blue precipitate, indicating hybridized probe.

While the PCR technique as presently practiced is an extremely powerful method for amplifying nucleic acid sequences, the detection of the amplified material requires additional manipulation and subsequent handling of the PCR products to determine whether the target DNA is present. It would be desirable to decrease the number of subsequent handling steps currently required for the detection of amplified material. A "homogeneous" assay system, that is, one which generates signal while the target sequence is amplified, requiring minimal post amplification handling, would be ideal.

DISCLOSURE OF THE INVENTION

The present invention provides a process for the detection of a target nucleic acid sequence in a sample, said process comprising:

(a) contacting a sample comprising single-stranded nucleic acids with an oligonucleotide containing a sequence complementary to a region of the target nucleic acid and a labeled oligonucleotide containing a sequence complementary to a second region of the same target nucleic acid strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3' end of the first oligonucleotide is adjacent to the 5' end of the labeled oligonucleotide;

(b) maintaining the mixture of step (a) with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments; and (c) detecting and/or measuring the release of labeled fragments.

This process is especially suited for analysis of nucleic acid amplified by PCR. This process is an improvement over known PCR detection methods because it allows for both amplification of a target and the release of a label for detection to be accomplished in a reaction system without resort to multiple handling steps of the amplified product. Thus, in another embodiment of the invention, a polymerase chain reaction amplification method for concurrent amplification and detection of a target nucleic acid sequence in a sample is provided. This method comprises:

(a) providing to a PCR assay containing said sample, at least one labeled oligonucleotide containing a sequence complementary to a region of the target nucleic acid, wherein said labeled oligonucleotide anneals within the target nucleic acid sequence bounded by the oligonucleotide primers of step (b);

(b) providing a set of oligonucleotide primers, wherein a first primer contains a sequence complementary to a region in one strand of the target nucleic acid sequence and primes the synthesis of a complementary DNA strand, and a second primer contains a sequence complementary to a region in a second strand of the target nucleic acid sequence and primes the synthesis of a complementary DNA strand; and wherein each oligonucleotide primer is selected to anneal to its complementary template upstream of any labeled oligonucleotide annealed to the same nucleic acid strand;

(c) amplifying the target nucleic acid sequence employing a nucleic acid polymerase having 5' to 3' nuclease activity as a template dependent polymerizing agent under conditions which are permissive for PCR cycling steps of (i) annealing of primers and labeled oligonucleotide to a template nucleic acid sequence contained within the target region, and (ii) extending the primer, wherein said nucleic acid polymerase synthesizes a primer extension product while the 5' to 3' nuclease activity of the nucleic acid polymerase simultaneously releases labeled fragments from the annealed duplexes comprising labeled oligonucleotide and its complementary template nucleic acid sequences, thereby creating detectable labeled fragments; and (d) detecting and/or measuring the release of labeled fragments to determine the presence or absence of target sequence in the sample.

MODES OF CARRYING OUT THE INVENTION

A. Definitions

Figure 1:
FIG. 1 is an autoradiograph of a DEAE cellulose thin layer chromatography (TLC) plate illustrating the release of labeled fragments from cleaved probe.

As used herein, a "sample" refers to a sample of tissue or fluid isolated from an individual or individuals, including but not limited to, for example, skin, plasma, serum, spinal fluid, lymph fluid, synovial fluid, urine, tears, blood cells, organs, tumors, and also to samples of in vitro cell culture constituents (including but not limited to conditioned medium resulting from the growth of cells in cell culture medium, recombinant cells and cell components).

As used herein, the terms "nucleic acid", "polynucleotide" and "oligonucleotide" refer to primers, probes, oligomer fragments to be detected, oligomer controls and unlabeled blocking oligomers and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA. The oligonucleotide is comprised of a sequence of approximately at least 6 nucleotides, preferably at least about 10-12 nucleotides, and more preferably at least about 15-20 nucleotides corresponding to a region of the designated nucleotide sequence. "Corresponding" means identical to or complementary to the designated sequence.

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature; and (3) is not found in nature.

Because mononucleotides are reacted to make oligonucleotides in a manner such that the 5= phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have a 5' and 3' ends.

When two different, non-overlapping oligonucleotides anneal to different regions of the same linear complementary nucleic acid sequence, the 3' end of one oligonucleotide points toward the 5' end of the other; the former may be called the "upstream" oligonucleotide and the latter the "downstream" oligonucleotide.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

Stability of a nucleic acid duplex is measured by the melting temperature, or "$T_m$." The $T_m$ of a particular nucleic acid duplex under specified conditions is the temperature at which half of the base pairs have disassociated.

As used herein, the term "target sequence" or "target nucleic acid sequence" refers to a region of the oligonucleotide which is to be either amplified, detected or both. The target sequence resides between the two primer sequences used for amplification.

As used herein, the term "probe" refers to a labeled oligonucleotide which forms a duplex structure with a sequence in the target nucleic acid, due to complementarity of at least one sequence in the probe with a sequence in the target region. The probe, preferably, does not contain a sequence complementary to sequence(s) used to prime the polymerase chain reaction. Generally the 3' terminus of the probe will be "blocked" to prohibit incorporation of the probe into a primer extension product. "Blocking" may be achieved by using non-complementary bases or by adding a chemical moiety such as biotin or even a phosphate group to the 3' hydroxyl of the last nucleotide, which may, depending upon the selected moiety, may serve a dual purpose by also acting as a label.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetric, X-ray diffraction or absorption, magnetism, enzymatic activity, and the like.

As defined herein, "5'→3' nuclease activity" or "5' to 3' nuclease activity" refers to that activity of a template-specific nucleic acid polymerase including either a 5'→3' exonuclease activity traditionally associated with some DNA polymerases whereby nucleotides are removed from the 5' end of an oligonucleotide in a sequential manner, (i.e., E. coli DNA polymerase I has this activity whereas the Klenow fragment does not), or a 5'→3" endonuclease activity wherein cleavage occurs more than one nucleotide from the 5' end, or both.

By "adjacent" as used herein refers to the positioning of the primer with respect to the probe on its complementary strand of the template nucleic acid. The primer and probe may be separated by 1 to about 20 nucleotides, more preferably, about 1 to 10 nucleotides, or may directly abut one another, as may be desirable for detection with a polymerization-independent process. Alternatively, for use in PCR amplification and detection methods as taught herein, the "adjacency" may be anywhere within the sequence to be amplified.

As used herein, the term "thermostable nucleic acid polymerase" refers to an enzyme which is relatively stable to heat when compared, for example, to nucleotide polymerases from E. coli and which catalyzes the polymerization of nucleosides. Generally, the enzyme will initiate synthesis at the 3'-end of the primer annealed to the target sequence, and will proceed in the 5'-direction along the template, and if possessing a 5' to 3' nuclease activity, hydrolyzing intervening, annealed probe to release both labeled and unlabeled probe fragments, until synthesis terminates. A representative thermostable enzyme isolated from *Thermus aquaticus* (Taq) is described in U.S. Pat. No. 4,889,818 and a method for using it in conventional PCR is described in Saiki et al., (1988), *Science* 239:487.

Taq DNA polymerase has a DNA synthesis-dependent, strand replacement 5'-3' exonuclease activity (see Gelfand, "Taq DNA Polymerase" in *PCR Technology: Principles and Applications for DNA Amplification*, Erlich, Ed., Stockton Press, N.Y. (1989), Chapter 2). In solution, there is little, if any, degradation of labeled oligonucleotides.

B. General Method

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Frtisch & Maniatis, *Molecular Cloning; A Laboratory Manual*, Second Edition (1989); *Oligonucleotide Synthesis* (M.J. Gait, ed., 1984); *Nucleic Acid Hybridization* (B.D Hames & S.J. Higgins, eds., 1984); *A Practical Guide to Molecular Cloning* (B. Perbal, 1984); and a series, *Methods in Enzymology* (Academic Press, Inc.). All patents, patent applications, and publications mentioned herein, both supra and infra, are hereby incorporated by reference.

The various aspects of the invention are based on a special property of nucleic acid polymerases. Nucleic acid polymerases are known to possess several activities, among them, a 5' to 3' nuclease activity whereby the nucleic acid polymerase can cleave mononucleotides or small oligonucleotides from an oligonucleotide annealed to its larger, complementary polynucleotide. In order for cleavage to occur, an upstream oligonucleotide must also be annealed to the same larger polynucleotide.

The 3' end of this upstream oligonucleotide provides the initial binding site for the nucleic acid polymerase. As soon as the bound polymerase encounters the 5' end of the downstream oligonucleotide, the polymerase can cleave mononucleotides or small oligonucleotides therefrom.

The two oligonucleotides can be designed such that they anneal in close proximity on the complementary target nucleic acid such that binding of the nucleic acid polymerase to the 3' end of the upstream oligonucleotide automatically puts it in contact with the 5' end of the downstream oligonucleotide. In this process, polymerization is not required to bring the nucleic acid polymerase into position to accomplish the cleavage, therefore we call this polymerization-independent cleavage.

Alternatively, if the two oligonucleotides anneal to more distantly spaced regions of the template nucleic acid target, polymerization must occur before the nucleic acid polymerase encounters the 5' end of the downstream oligonucleotide. As the polymerization continues, the polymerase progressively cleaves mononucleotides or small oligonucleotides from the 5' end of the downstream oligonucleotide. This cleaving continues until the remainder of the downstream oligonucleotide has been destabilized to the extent that it dissociates from the template molecule. We call this process polymerization-dependent cleavage.

In the present invention, a label is attached to the downstream oligonucleotide. Thus, the cleaved mononucleotides or small oligonucleotides which are cleaved by the 5'-3' nuclease activity of the polymerase can be detected.

Subsequently, any of several strategies may be employed to distinguish the uncleaved labeled oligonucleotide from the cleaved fragments thereof. In this manner, the present invention permits identification of those nucleic acid samples which contain sequences complementary to the upstream and downstream oligonucleotides.

The present invention exploits this 5' to 3' nuclease activity of the polymerase when used in conjunction with PCR. This differs from previously described PCR amplification wherein the post-PCR amplified target oligonucleotides are detected, for example, by hybridization with a probe which forms a stable duplex with that of the target sequence under stringent to moderately stringent hybridization and wash conditions. In contrast to those known detection methods used in post-PCR amplifications, the present invention permits the detection of the target nucleic acid sequences during amplification of this target nucleic acid. In the present invention, a labeled oligonucleotide is added concomitantly with the primer at the start of PCR, and the signal generated from hydrolysis of the labeled nucleotide(s) of the probe provides a means for detection of the target sequence during its amplification.

One advantage of the polymerization-independent process lies in the elimination of the need for amplification of the target sequence. In the absence of primer extension, the target nucleic acid is substantially single-stranded. Provided the primer and labeled oligonucleotide are adjacently bound to the target nucleic acid, sequential rounds of oligonucleotide annealing and cleavage of labeled fragments can occur. Thus, a sufficient amount of labeled fragments can be generated, making detection possible in the absence of polymerization. As would be appreciated by those skilled in the art, the signal generated during PCR amplification could be augmented by this polymerization-independent activity.

In either process described herein, a sample is provided which is suspected of containing the particular oligonucleotide sequence of interest, the "target nucleic acid". The target nucleic acid contained in the sample may be first reverse transcribed into cDNA, if necessary, and then denatured, using any suitable denaturing method, including physical, chemical, or enzymatic means, which are known to those of skill in the art. A preferred physical means for strand separation involves heating the nucleic acid until it is completely (>99%) denatured. Typical heat denaturation involves temperatures ranging from about 80° C. to about 105° C., for times ranging from about 1 to 10 minutes. As an alternative to denaturation, the target nucleic acid may exist in a single-stranded form in the sample, such as, for example, single stranded RNA or DNA viruses.

The denatured nucleic acid strands are then incubated with preselected oligonucleotide primers and labeled oligonucleotide (also referred to herein as "probe") under hybridization conditions, conditions which enable the binding of the primers and probes to the single nucleic acid strands. As known in the art, the primers are selected so that their relative positions along a duplex sequence are such that an extension product synthesized from one primer, when the extension produce is separated from its template (complement), serves as a template for the extension of the other primer to yield a replicate chain of defined length.

Because the complementary strands are longer than either the probe or primer, the strands have more points of contact and thus a greater chance of finding each other over any given period of time. A high molar excess of probe, plus the primer, helps tip the balance toward primer and probe annealing rather than template reannealing.

The primer must be sufficiently long to prime the synthesis of extension products in the presence of the agent for polymerization. The exact length and composition of the primer will depend on many factors, including temperature of the annealing reaction, source and composition of the primer, proximity of the probe annealing site to the primer annealing site, and ratio of primer:probe concentration. For example, depending on the complexity of the target sequence, the oligonucleotide primer typically contains about 15-30 nucleotides, although it may contain more or fewer nucleotides. The primers must be sufficiently complementary to selectively anneal to their respective strands and form stable duplexes.

The primers used herein are selected to be "substantially" complementary to the different strands of each specific sequence to be amplified. The primers need not reflect the exact sequence of the template, but must be sufficiently complementary to selectively hybridize to their respective strands. Non complementary bases or longer sequences can be interspersed into the primer or located at the ends of the primer, provided the primer retains sufficient complementarity with its template strand to form a stable duplex therewith. The non complementary nucleotide sequences of the primers may include restriction enzyme sites.

In the practice of the invention, the labeled oligonucleotide must be first annealed to its complementary nucleic acid before the nucleic acid polymerase encounters region, thereby permitting the 5' to 3' nuclease activity to cleave and release labeled oligonucleotide fragments.

To enhance the likelihood that the labeled oligonucleotide will have annealed to its complementary nucleic acid before primer extension polymerization reaches this duplex region, or before the polymerase attaches to the upstream oligonucleotide in the polymerization-independent process, a variety of techniques may be employed. Short primer molecules generally require cooler temperature to form sufficiently stable hybrid complexes with the target nucleic acid. Therefore, the labeled oligonucleotide can be designed to be longer than the primer so that the labeled oligonucleotide anneals preferentially to the target at higher temperatures relative to primer annealing.

One can also use primers and labeled oligonucleotides having differential thermal stability. For example, the nucleotide composition of the labeled oligonucleotide can be chosen to have greater G/C content and, consequently, greater thermal stability than the primer. The thermocycling parameters can also be varied to take advantage of the differential thermal stability of the labeled oligonucleotide and primer. For example, following the denaturation step in thermocycling, an intermediate temperature may be introduced which is permissible for labeled oligonucleotide binding but not primer binding, and then the temperature is further reduced to permit primer annealing and extension.

To preferentially favor binding of the labeled oligonucleotide before the primer, a high molar excess of labeled oligonucleotide to primer concentration can also be used. Such labeled oligonucleotide concentrations are typically in the range of about 2 to 20 times higher than the respective primer concentration, which is generally $0.5-5\times10^{-7}$ M.

The oligonucleotide primers and labeled oligonucleotides may be prepared by any suitable method. Methods for preparing oligonucleotides of specific sequence are known in the art, and include, for example, cloning and restriction of appropriate sequences, and direct chemical synthesis. Chemical synthesis methods may include, for example, the phosphotriester method described by Narang et al. (1979) *Methods in Enzymology* 68:90, the phosphodiester method disclosed by Brown et al. (1979) *Methods in Enzymology* 68:109, the diethylphosphoramidate method disclosed in Beaucage et al. (1981) *Tetrahedron Letters* 22:1859, and the solid support method disclosed in U.S. Pat. No. 4,458,066.

The composition of the labeled oligonucleotide can be designed to favor nuclease activity over strand displacement (mono- and dinucleotide fragments over oligonucleotides) by means of choice of sequences which are GC rich or which avoid sequential A's and T's and by choice of label position in the probe. It has been determined that in the presence of AT rich sequences in the 5' complementary probe region, cleavage occurs after the approximately fourth, fifth or sixth nucleotide. However, in a GC-rich 5' complementary probe region, cleavage generally occurs after the first or second nucleotide. Alternatively, the incorporation of modified phosphodiester linkages (e.g., methyl phosphorylthioate or methylphosphonates) in the labeled probe during chemical synthesis (Noble et al., (1984) *Nuc Acids Res* 12:3387-3403; Iyer et al., (1990) *J Am Chem Soc* 112:1253-1254) may be used to prevent cleavage at a selected site. Depending on the length of the probe, the composition of its 5' complementary region, and the position of the label, one can design a probe to preferentially favor the generation of short or long labeled probe fragments for use in the practice of the invention.

The oligonucleotide is labeled, as described below, by incorporating moieties detectable by spectroscopic, photochemical, biochemical, immunochemical, or chemical means. The method of linking or conjugating the label to the oligonucleotide probe depends, of course, on the type of label(s) used and the position of the label on the probe.

A variety of labels which would be appropriate for use in the invention, as well as methods for their inclusion in the probe, are known in the art and include, but are not limited to, enzymes (e.g., alkaline phosphatase and horseradish peroxidase) and enzyme substrates, radioactive atoms, fluorescent dyes, chromophores, chemiluminescent labels, electrochemiluminescent labels, such as Origin ™ (Igen), ligands having specific binding partners, or any other labels that may interact with each other to enhance, alter, or diminish a signal. Of course, should the PCR be practiced using a Thermo Cycler instrument, the label must be able to survive the temperature cycling required in this automated process.

Among radioactive atoms, $^{32}$P is preferred. Methods for introducing $^{32}$P into nucleic acids are known in the art, and include, for example, 5' labeling with a kinase, or random insertion by nick translation. Enzymes are typically detected by their activity. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}$I may serve as a radioactive label or as an electron-dense reagent. HRP may serve as enzyme or as antigen for a monoclonal antibody. Further, one may combine various labels for desired effect. For example, one might label a probe with biotin, and detect its presence with avidin labeled with $^{125}$I, or with an anti-biotin monoclonal antibody labeled with HRP. Other permutations and possibilities will be readily apparent to those of ordinary skill in the art, and are considered as equivalents within the scope of the instant invention.

In some situations it may be desirable to use two interactive labels on a single oligonucleotide with due consideration given for maintaining an appropriate spacing of the labels on the oligonucleotide to permit the separation of the labels during oligonucleotide hydrolysis, and in other instances it may be desirable to use a single probe having two different label moieties. In this embodiment of the invention, detection of the hydrolyzed labeled probe can be accomplished using, for example, fluorescence polarization. This technique is able to differentiate between large and small molecules based on molecular tumbling. Large molecules (e.g., intact labeled probe) tumble in solution much more slowly than small molecules. Upon linkage of a fluorescent moiety to the molecule of interest (e.g., the 5' end of a labeled probe), this fluorescent moiety can be measured (and differentiated) based on molecular tumbling, thus differentiating between intact and digested probe. Detection may be measured directly during PCR or may be performed post PCR.

In yet another embodiment, two labelled oligonucleotides are used, each complementary to separate regions of a double-stranded target region, but not to each other, oligonucleotide designed to anneal downstream of its respective primer. For example, the presence of two probes can potentially double the intensity of the signal generated from a single label and may further serve to reduce product strand reannealing, as often occurs during PCR amplification. The probes are selected so that their relative positions are adjacent to their respective primers.

The labels may be attached to the oligonucleotide directly or indirectly by a variety of techniques. Depending on the precise type of label used, the label might be located at the 5' or 3' end of the probe, located internally in the probe's nucleotide sequence, or attached to spacer arms of various sizes and compositions to facilitate signal interactions. Using commercially available phosphoramidite reagents, one can produce oligomers containing functional groups (e.g., thiols or primary amines) at either terminus via an appropriately protected phosphoramidite, and can label them using protocols described in, for example, PCR Protocols: A Guide to Methods and Applications, ed. by Innis et al., Academic Press, Inc., 1990.

Methods for introducing oligonucleotide functionalizing reagents to introduce one or more sulfhydryl, amino or hydroxyl moieties into the oligonucleotide probe sequence, typically at the 5' terminus are described in U.S. Pat. No. 4,914,210. A 5' phosphate group can be introduced as a radioisotope by using polynucleotide kinase and [gamma$^{32}$P]ATP to provide a reporter group. Biotin can be added to the 5' end by reacting an aminothymidine residue, introduced during synthesis, with an N-hydroxysuccinimide ester of biotin.

Labels at the 3' terminus may employ polynucleotide terminal transferase to add the desired moiety, such as for example, cordycepin $^{35}$S-dATP, and biotinylated dUTP.

Oligonucleotide derivatives are also available labels. For example, etheno-dA and etheno-A are known fluorescent adenine nucleotides which can be incorporated into an oligonucleotide probe. Similarly, etheno-dC is another analog that could be used in probe synthesis. The probes containing such nucleotide derivatives may be hydrolyzed to release much more strongly fluorescent mononucleotides by the polymerase's 5' to 3' nuclease activity as DNA polymerase extends a primer during PCR.

Template-dependent extension of the oligonucleotide primer(s) is catalyzed by a polymerizing agent in the presence of adequate amounts of the four deoxyribonucleoside triphosphates (dATP, dGTP, dCTP, and dTTP) or analogs as discussed above, in a reaction medium which is comprised of the appropriate salts, metal cations, and pH buffering system. Suitable polymerizing agents are enzymes known to catalyze primer and template-dependent DNA synthesis and possess the 5' to 3' nuclease activity. Known DNA polymerases include, for example, E. coli DNA polymerase I, Thermus thermophilus (Tth) DNA polymerase, Bacillus stearothermophilus DNA polymerase, Thermococcus littoralis DNA polymerase, and Thermus aquaticus (Taq) DNA polymerase. The reaction conditions for catalyzing DNA synthesis with these DNA polymerases are well known in the art. To be useful in the present invention, the polymerizing agent must efficiently cleave the oligonucleotide and release labeled fragments so that the signal is directly or indirectly generated.

The products of the synthesis are duplex molecules consisting of the template strands and the primer extension strands, which include the target sequence. By-products of this synthesis are labeled oligonucleotide fragments which consist of a mixture of mono-, di- and larger nucleotide fragments. Repeated cycles of denaturation, labeled oligonucleotide and primer annealing, and primer extension and cleavage of the labeled oligonucleotide result in the exponential accumulation of the target region defined by the primers and the exponential generation of labeled fragments. Sufficient cycles are run to achieve a detectable species of label, which is generally several orders of magnitude greater than background signal.

In a preferred method, the PCR reaction is carried out as an automated process which utilizes a thermostable enzyme. In this process the reaction mixture is cycled through a denaturing step, a probe and primer annealing step, and a synthesis step, whereby cleavage and displacement occurs simultaneously with primer dependent template extension. A DNA thermal cycler, such as the commercially available machine from Perkin-Elmer Cetus Instruments, which is specifically designed for use with a thermostable enzyme, may be employed.

Temperature stable polymerases are preferred in this automated process because the preferred way of denaturing the double stranded extension products is by exposing them to a high temperature (about 95° C.) during the PCR cycle. For example, U.S. Pat. No. 4,889,818 discloses a representative thermostable enzyme isolated from Thermus aquaticus. Additional representative temperature stable polymerases include, e.g., polymerases extracted from the thermostable bacteria Thermus flavus, Thermus ruber, Thermus thermophilus, Bacillus stearothermophilus (which has a somewhat lower temperature optimum than the others listed), Thermus lacteus, Thermus rubens, Thermotoga maritima, Thermococcus littoralis, and Methanothermus fervidus.

Detection or verification of the labeled oligonucleotide fragments may be accomplished by a variety of methods and may be dependent on the source of the label or labels employed. One convenient embodiment of the invention is to subject the reaction products, including the cleaved label fragments to size analysis. Methods for determining the size of the labeled nucleic acid fragments are known in the art, and include, for example, gel electrophoresis, sedimentation in gradients, gel exclusion chromatography and homochromatography.

During or after amplification, separation of the labeled fragments from the PCR mixture can be accomplished by, for example, contacting the PCR mixture with a solid phase extractant (SPE). For example, materials having an ability to bind oligonucleotides on the basis of size, charge or interaction with the oligonucleotide bases can be added to the PCR mixture, under conditions where labeled, uncleaved oligonucleotides are bound and labeled fragments are not. Such SPE materials include ion exchange resins or beads, such as the commercially available binding particles Nensorb ™ (DuPont Chemical Co., Nucleogen ™ (The Nest Group) and hydroxylapatite. In a specific embodiment, if a dual labeled oligonucleotide comprising a 3' biotin label separated from a 5' label by a nuclease susceptible cleavage site is employed as the signal means, the PCR amplified mixture can be contacted with materials containing a specific binding partner such as avidin or streptavidin, or an antibody or monoclonal antibody to biotin. Such materials can include beads and particles coated with specific binding partners and can also include magnetic particles.

Following the step wherein the PCR mixture has been contacted with a SPE, the SPE material can be removed by filtration, sedimentation or magnetic attraction leaving the labeled fragments free of uncleaved labeled oligonucleotides and available for detection.

Reagents employed in the methods of the invention can be packaged into diagnostic kits. Diagnostic kits include the labeled oligonucleotides and the primers in separate containers. If the oligonucleotide is unlabeled, the specific labeling reagents may also be included in the kit. The kit may also contain other suitably packaged reagents and materials needed for amplification, for example, buffers, dNTPs, and/or polymerizing means, and for detection analysis, for example, enzymes and solid phase extractants, as well as instructions for conducting the assay.

EXAMPLES

The examples presented below are intended to be illustrative of the various methods and compounds of the invention.

```
BW31 = 5' 5541-5512 3'
       5'-*CGCTGCGCGTAACCACCACACCCGCCGCGCX-3'

BW33 = 5' 5541-5512 3'
       5'-*gatCGCTGCGCGTAACCACCACACCCGCCGCCGCGCX-3'

BW35 = 5' 5541-5512 3'
       5'-*cgtcaccgatCGCTGCGCGTAACCACCACACCCGCCGCGCX-3'
```

X = 3'-phosphate
a, t, g, c, = bases non-complementary to template strand
* = gamma $^{32}$P-ATP label

Example I: PCR Probe Label Release

A PCR amplification was performed which liberated the 5' $^{32}$P-labeled end of a complementary probe when specific intended product was synthesized.

A Labeling of probe with gamma $^{32}$P-ATP and polynucleotide kinase

Ten pmol of each probe (BW31, BW33, BW35, sequences provided below) were individually mixed with fifteen units of T4 polynucleotide kinase (New England Biolabs) and 15.3 pmol of gamma $^{32}$P-ATP (New England Nuclear, 3000 Ci/mmol) in a 50 ul reaction volume containing 50 mM Tris HCl, pH 7.5, 10 mM MgCl$_2$, 5 mM dithiothreitol, 0.1 mM spermidine and 0.1 mM EDTA for 60 min at 37° C. The total volume was then phenol/chloroform extracted, and ethanol precipitated as described by Sambrook, et al., *Molecular Cloning*, Second Edition (1989). Probes were resuspended in 100 ul TE buffer and run over a Sephadex G-50 spin dialysis column to remove unincorporated gamma $^{32}$P-ATP as taught in Sambrook et al., supra. TCA precipitation of the reaction products indicated the following specific activities:

BW31: 1.98×10$^6$ cpm/pmol

BW33: 2.54×10$^6$ cpm/pmol

BW35: 1.77×10$^6$ cpm/pmol

Final concentration of all three probes was 0.10 pmol/ul.

B. Amplification

The amplified region was a 350 base pair product from the bacteriophage M13mp10w directed by primers BW36 and BW42. The region of each numbered primer sequence designated herein, follows standard M13 nucleotide sequence usage.

```
BW36 =
    5' 5241-5268 3'
    5'-CCGATAGTTTGAGTTCTTCTACTCAGGC-3'
```

```
-continued
BW42 =
    5' 5591-5562 3'
    5'-GAAGAAAGCGAAAGGAGCGGGCGCTAGGGC-3'
```

Three different probes were used, which contained the exact 30 base complementary sequence to M13mp10w, but differed in the lengths of their non complementary 5' tail regions. Probes were synthesized to have a 3'-PO$_4$ instead of a 3'-OH to block any extension by Taq polymerase.

For amplification of the 350 bp fragment, 10$^{-3}$ pmol of target M13mp10w sequence were added to a 50 ul reaction volume containing 50 mM KCl, 10 mM Tris HCl pH 8.3, 3 mM MgCl$_2$, 10 pmol each of primers BW36 and BW42, 200 uM each of four deoxynucleoside triphosphates, 1.25 units Taq DNA polymerase and either 1, 10 or 20 pmol of isotopically diluted probe BW31, BW33 or BW35.

The amount of radiolabeled probe was held constant at 0.4 pmol per reaction and diluted to 1, 10 or 20 pmol with non-radioactive probe.

Taq polymerase was added as 4 ul per reaction at 0.3125 U/ul and diluted in 10 mM Tris-HCl pH 8.0, 50 mM KCl, 0.1 mM EDTA, 0.5% NP40+0.5% Tween 20, and 500 ug/ml gelatin.

A master reaction mix was made containing appropriate amounts of reaction buffer, nucleoside triphosphates, both primers and enzyme. From this master mix aliquots were taken and to them were added template and various concentrations of each probe. Control reactions consisted of adding all reaction components except template, and all reaction components except probe. Each reaction mixture was overlayed with 50 ul mineral oil to prevent evaporation, microcentrifuged for 45 seconds, and then placed into a thermal cycler. Reaction mixtures were subjected to the following amplification scheme:

| | |
|---|---|
| Fifteen cycles: | 96° C. denaturation, 1 min |
| | 60° C. anneal/extension, 1.5 min |
| One cycle: | 96° C. denaturation, 1 min |
| | 60° C. anneal/extension, 5.5 min |

After cycling, the mineral oil was extracted with 50 ul chloroform, the mixtures were stored at 4° C. and the following tests were performed.

C. Analysis

For acrylamide gel analysis, 4 ul of each amplification reaction were mixed with 3 ul 5X gel loading mix (0.125% bromophenol blue, 12.5% Ficoll 400 in H$_2$O) and loaded onto a 4% acrylamide gel (10 ml of 10X TBE buffer, 1 ml 10% ammonium persulfate, 10 ml 40% Bis Acrylamide 19:1, 50 ul TEMED, and 79 ml H$_2$O) in 1X TBE buffer (0.089M Tris, 0.089M boric acid, and 2 mM EDTA) and electrophoresed for 90 min at 200 volts. After staining with ethidium bromide, DNA was visualized by UV fluorescence.

The results showed that the presence of each of these three probes at the various concentrations had no effect on the amount of amplified product generated. Sample lanes containing no probe showed discrete high intensity 350 base pair bands corresponding to the desired sequence. All lanes containing probe showed the same, as well as a few faint bands at slightly higher molecular weight. Control lanes without template added showed no bands whatsoever at 350 bases, only lower intensity bands representing primer at 30-40 bases.

After photographing, the gel was transferred onto Whatman paper, covered with Saran Wrap and autoradiographed. An overnight exposure revealed that 90-95% of the radiolabel was near the bottom of the gel, where probe or partially degraded probe would run.

For the denaturing gel analysis, 2 ul of each amplification reaction were mixed with 2 ul formamide loading buffer (0.2 ml 0.5M EDTA pH 8, 10 mg bromophenol blue, 10 mg xylene cyanol, 10 ml formamide), then heated to 96° C. for 3-5 min and placed on ice. Samples were loaded onto a 6.2% denaturing gradient polyacrylamide gel (7M urea with both a sucrose and a buffer gradient) according to the procedure of Sambrook et al., supra. The gel was electrophoresed for 90 min at 2000 V, 45 W, then transferred onto Whatman paper and autoradiographed.

Results from the denaturing gel indicated that about 50% of each probe was degraded into smaller labeled fragments. Approximately 50%-60% of the counts lie in the 30-40 base range, corresponding to undergraded probe. A very faint band is visible at 300 bases for all the amplification reactions, suggesting that a very small percentage of the probes have lost their 3'PO$_4$ group and have been extended. The remainder of the counts are in the range of zero to fifteen bases. The resolution on such a gel does not reveal the exact size of products. This can be better noted by homochromatography analysis.

For a homochromatography analysis, 1 ul of each sample was spotted 1.2 cm apart onto a Polygram CEL 300 DEAE 20×20 cm cellulose thin layer plate, which was pre-spotted with 5 ul sheared herring sperm DNA (150 ug/ml) and allowed to dry. After the sample was dried, the plate was placed in a trough with distilled H$_2$O, and the water allowed to migrate just above the sample loading area. The plate was then placed in a glass development tank containing filtered Homo mix III (Jay et al., (1979) *Nuc Acids Res* 1(3):331-353), a solution of partially hydrolized RNA containing 7M urea, in a 70° C. oven.

The Homo-Mix was allowed to migrate by capillary action to the top of the plate, at which time the plate was removed, allowed to dry, covered with Saran Wrap, and then autoradiographed.

An overnight exposure of the homochromatography plate also indicated that about 40% of the probes were degraded into smaller fragments. These fragments were very specific in size, depending upon the length of the 5' non-complementary tail of each probe. FIG. 1 shows an autoradiograph of the TLC plate. Probe BW31 (Lanes 1-3) which was fully complementary to the M13mp10w template, generated labeled fragments predominantly one to two bases long. Probe BW33, (Lanes 4-6) containing a 5' 3 base non-complementary region, released products predominantly four to six bases long. BW35 (Lanes 7-9) had a 5' 10 base non-complementary tail and released products predominantly 12 to 13 bases in length. Lanes 10-12 are control reactions containing either BW31, BW33 or BW35 and all PCR components except template after 15 cycles. During DNA synthesis, the enzyme displaced the first one or two paired bases it encountered and then cut at that site, indicative of an endonuclease-like activity. The results show specific probe release coordinately with product accumulation in PCR.

Example II: Specificity of Probe Label Release

The specificity of labeled probe release was examined by performing a PCR amplification using bacteriophage lambda DNA and primers, and a series of non-complementary kinased probes.

The region to be amplified was a 500 nucleotide region on whole bacteriophage lambda DNA from the GeneAmp ® DNA Amplification Reagent kit (Perkin-Elmer Cetus), flanked by primers PCRO1 and PCRO2, also from the GeneAmp ® DNA kit.

PCRO1 = 5' 7131-7155 3'
5'-GATGAGTTCGTGTCCGTACAACTGG-3'

PCRO2 = 5' 7630-7606 3';
5'-GGTTATCGAAATCAGCCACAGCGCC-3'

Aliquots of the same three labeled probes BW31, BW33 and BW35 identified in Example I, were used, all of which were entirely non-complementary to the target sequence.

For amplification of the 500 base pair region, 0.5 ng of target lambda DNA sequence (control Template, Lot #3269, 1 ug/ml, dilute 1:10 in 10 mM Tris-HCl pH 8.0, 1 mM EDTA, 10 mM NaCl for stock) were added to a 50 ul reaction volume containing 50 mM KCl, 10 mM Tris-HCl pH 8.3, 3 mM MgCl$_2$, 1 uM each of primers PCRO1 (Lot #3355) and PCRO2 (Lot #3268), 200 uM each of four deoxynucleoside triphosphates, 1.25 units Taq DNA polymerase, and either 2, 10 or 20 pmol of isotopically diluted probe BW31, BW33 or BW35.

The amount of radiolabeled probe was held constant to 0.4 pmol per reaction and diluted to 1, 10 or 20 pmol with non-radioactive probe.

Taq DNA polymerase was added as 4 ul per reaction at 0.3125 units/ul and diluted in 10 mM Tris-HCl pH 8.0, 50 mM KCl, 0.1 mM EDTA, 0.5% NP40+0.5% Tween 20, and 500 ug/ml gelatin.

The master reaction mix was made as previously taught, along with the control reactions minus probe or minus enzyme. The reaction mixtures were amplified following the cycling conditions set forth in Example 1B and then analyzed as follows.

For acrylamide gel analysis, 4 ul of each amplification reaction mixed with 3 ul 5X loading mix were loaded onto a 4% acrylamide gel in 1X TBE buffer and electrophoresed for 90 min at 200 volts. After staining with ethidium bromide, DNA was visualized by UV fluorescence.

The results show that the presence of any probe at any concentration has no effect on the amount of amplified product generated. Sample control lanes containing no probe, and all lanes containing probe, showed a discrete high intensity 500 base pair band corresponding to the desired sequence. Control lanes with no enzyme added did not show any product bands but only low intensity bands representing primer and probe of approximately 30–40 nucleotides.

Figure 2:
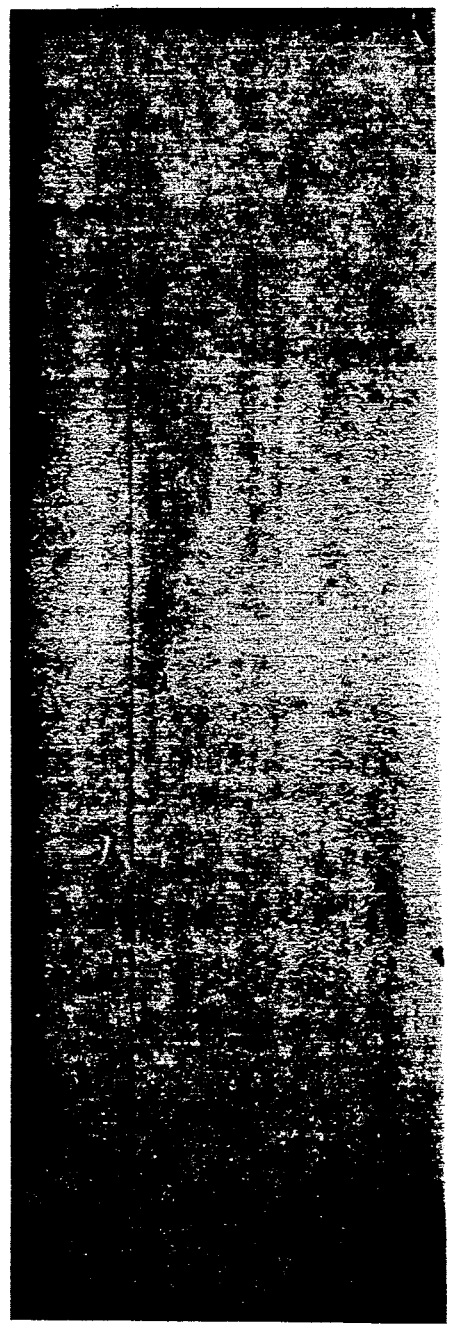
FIG. 2 is an autoradiograph of DEAE cellulose TLC plates illustrating the thermostability of the labeled probe.

The homochromatography analysis provided in FIG. 2 shows an overnight exposure of the plate in which no degradation of the probes was observed. All of the counts were located at the point of origin, showing no release of labeled fragments. Lanes 1–3 are reactions containing probe BW31; Lanes 4–6 include probe BW33; Lanes 7–9 include probe BW35; and Lanes 10–12 are control reactions without template. This data show that the probe is not degraded unless specifically bound to target, and is able to physically withstand the PCR cycling conditions.

In the denaturing gel analysis, 2 ul of each amplification reaction were mixed with 2 ul formamide loading buffer (described in Example I) and placed on a heat block at 96° C. for 3–5 min. Samples were immediately placed on ice and loaded onto a 6.2% denaturing gradient acrylamide gel, and electrophoresed for 90 min at 2000 volts. After electrophoresis, the gel was transferred onto Whatman paper, covered with Saran Wrap and autoradiographed.

An overnight exposure revealed all of the counts in the 30–40 base pair range, corresponding to the sizes of the probes. Once again there was no probe degradation apparent, further confirming that probe must be specifically bound to template before any degradation can occur.

Example III: Specificity of Probe Label Release in the Presence of Genomic DNA

In this example, the specificity of probe label release was examined by performing a PCR amplification in the presence of degraded or non-degraded human genomic DNA.

The BW33 kinased probe used in this experiment had a specific activity of $5.28 \times 10^6$ cpm/pmol determined by TCA precipitation following the kinasing reaction. The region amplified was the 350 base pair region of M13mp10w, flanked by primers BW36 and BW42. Primer sequences and locations are listed in Example I. Human genomic DNA was from cell line HL60 and was used undergraded or degraded by shearing in a french press to an average size of 800 base pairs.

Each 50 ul amplification reaction consisted of $10^{-2}$ or $10^{-3}$ pmol of M13mp10w target sequence, 1 ug either degraded or non-degraded HL60 genomic DNA added to a mixture containing 50 mM KCl, 10 mM Tris HCl pH 8.3, 3 mM MgCl$_2$, 10 pmol each of primers BW36 and BW42, 200 uM each of four deoxynucleoside triphosphates, 1.25 units Taq DNA polymerase and 10 pmol of isotopically diluted probe BW33.

A master reaction mix was made containing appropriate amounts of reaction buffer, nucleoside triphosphates, primers, probe and enzyme. Aliquots were made and to them was added M13mp10w template and/or genomic DNA. Control reactions included all reaction components except M13mp10w target DNA, or all reaction components except genomic DNA.

Each reaction mixture was overlaid with 50 ul mineral oil, microcentrifuged and placed into a thermal cycler. Reaction mixtures were subjected to the following amplification scheme:

For 10, 15 or 20 cycles: 96° C. denaturation, 1 min
60° C. anneal/extension, 1.5 min
Final cycle: 96° C. denaturation, 1 min
60° C. anneal/extension, 5.5 min After cycling, the mineral oil was extracted using 50 ul chloroform and samples were stored at 4° C.

Samples were subsequently analyzed by a 4% acrylamide gel electrophoresis, and homochromatography analysis.

For the acrylamide gel analysis, 4 ul of each reaction mixture were mixed with 3 ul 5X gel loading mix, loaded onto a 4% acrylamide gel in 1X TBE buffer, and electrophoresed for 90 min at 220 volts. DNA was visualized by UV fluorescence after staining with ethidium bromide.

In the lanes corresponding to control samples containing no M13mp10w target DNA, there were no visible product bands, indicating the absence of any cross-over contamination of M13mp10w. All subsequent lanes showed a band at 350 bases corresponding to the expected sequence. The intensity of the band was greater when $10^{-2}$ pmol M13mp10w target DNA was present over $10^{-3}$ pmol in the absence or presence of genomic DNA (degraded or undergraded). The product band intensity increased with increasing number of amplification cycles. Twenty cycles produced a band twice the intensity of that seen at ten cycles, and fifteen cycles generated a band of intermediate intensity. The amount of PCR product present varied on the amount of starting target template and the number of cycles, and the presence of 1 ug of human genomic DNA, whether degraded or undergraded, showed no effect at all on this product formation.

Figure 3A:
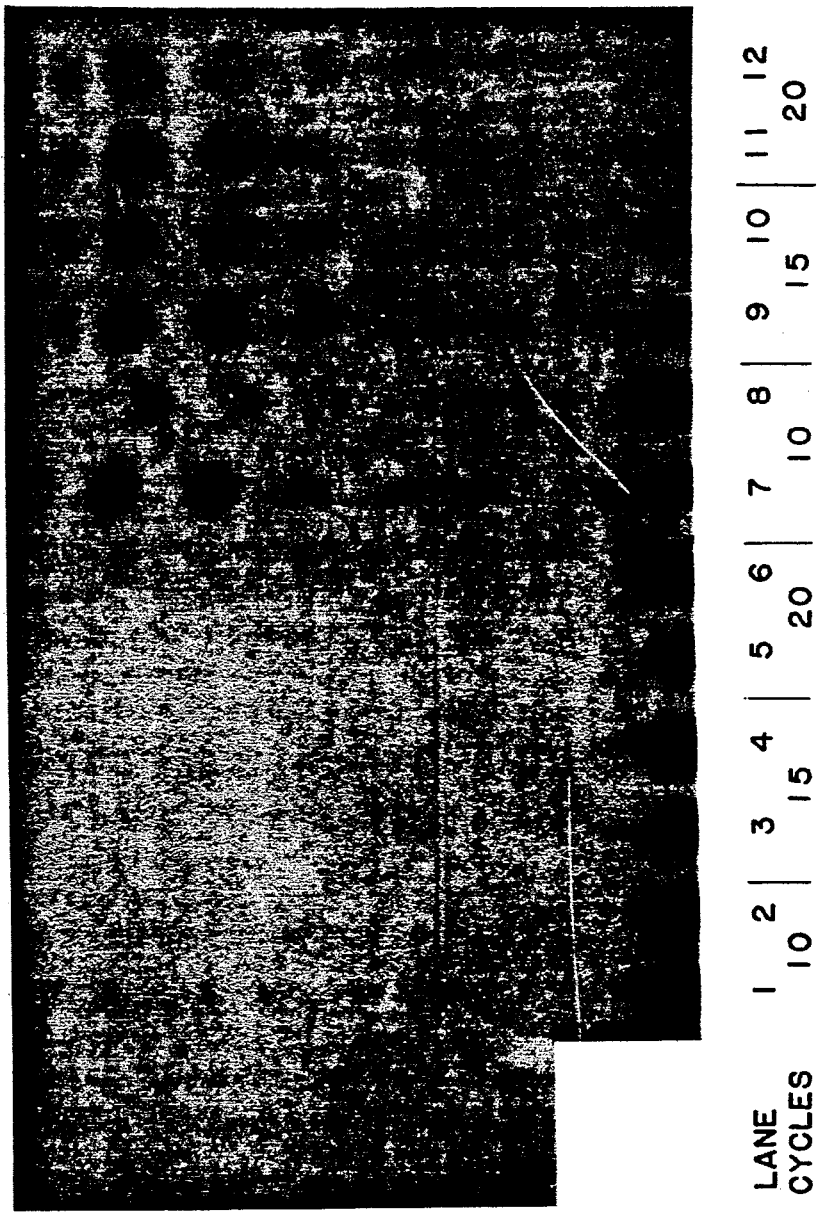
FIGS. 3A and 3B are autoradiographs of DEAE cellulose TLC plates showing that the amount of labeled probe fragment released correlates with an increase in PCR cycle number and starting template DNA concentration.
Figure 3B:
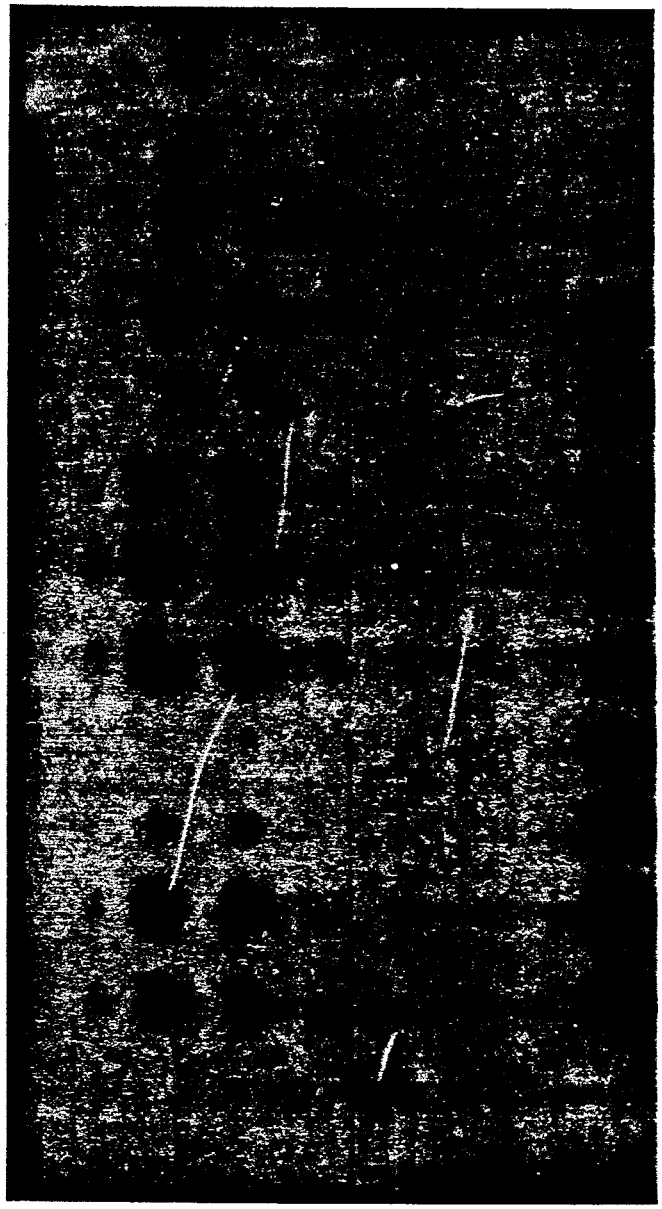

In the homochromatography analysis, 1 ul of each reaction mixture was spotted onto a DEAE thin layer plate, and placed in a developing chamber containing Homo-Mix III at 70° C. After 90 min, the plate was removed, allowed to dry, covered with Saran Wrap, and autoradiographed. An overnight exposure is shown in FIG. 3; in FIG. 3A, Lanes 1 to 6 show PCR reaction cycles in the absence of M13mp10w template DNA containing, alternately, degraded and undergraded HL60 DNA at 10, 15 and 20 cycles; and Lanes 7–12 are duplicate loading control reactions containing M13mp10w template DNA without any human genomic DNA at 10, 15 and 20 cycles. In FIG. 3B, reactions are amplified over increasing 5 cycle increments starting at 10 cycles. The M13mp10w template DNA concentration in the reactions shown in Lanes 1, 2, 5, 6, 9 and 10 is $10^{-2}$ pmol, while in lanes 3, 4, 7, 8, 11 and 12 is $10^{-3}$ pmol. The reactions shown in the odd numbered lanes from 1 through 1 contain degraded human genomic DNA and the even numbered lanes contain non-degraded human genomic DNA. Labeled probe fragments were seen as two well-defined spots migrating at approximately 4 and 5 bases in length on the thin layer plate. As the starting template concentration increased and/or as the cycle number increased, the amount of released labeled probe fragments also increased. The presence or absence of degraded or non degraded human genomic DNA did not interfere with or enhance probe hybridization and degradation.

The results show that increased amounts of released small probe fragments occur coordinately and simultaneously with specific product accumulation during the course of a PCR assay. The presence or absence of either a large amount of high complexity human genomic DNA or a large number of random DNA "ends"

has no effect on specific product accumulation or degree of probe release. Finally, the presence of a large amount of high complexity human genomic DNA does not lead to any detectable probe release in the absence of specific product accumulation.

Example IV: PCR with 3' Labeled Probe

A PCR amplification was performed which liberated a hybridized 3' radiolabeled probe into smaller fragments when the probe was annealed to template. The sequences of the probes were as follows:

DG46 = 5' 5541-5512-3'
5'-CGCTGCGCGTAACCACCACACCCGCCGCGC-3'

BW32 = 5' 5541-5512-3'
5'-gatCGCTGCGCGTAACCACCACACCCGCCGCGC-3'

BW34 = 5' 5541-5512-3'
5'-cgtcaccgatCGCTGCGCGTAACCACCACACCCGCCGCGC-3'

A. Labeling of Probes with $^{32}$P-cordycepin and terminal transferase

Five pmol of each probe (DG46, BW32, BW34) were individually mixed with 17.4 units of terminal transferase (Stratagene) and 10 pmol cordycepin (cordycepin: 3'-deoxyadenosine-5'-triphosphate, New England Nuclear, 5000 Ci/mmol, diluted 3X with ddATP [Pharmacia]) in a 17.5 ul reaction volume containing 100 mM potassium cacodylate, 25 mM Tris-HCl pH 7.6, 1 mM CoCl$_2$, and 0.2 mM dithiothreitol for 60 min at 37° C. The total volume was then phenol/chloroform extracted and ethanol precipitated. Probes were resuspended in 50 ul TE buffer and run over a Sephadex G-50 spin dialysis column according to the procedure of Sambrook, et al., Molecular Cloning, supra. The final concentration of probes was 0.1 pmol/ul. TCA precipitation of the reaction products indicated the following specific activities:

$DG46$: $2.13 \times 10^6$ cpm/pmol $BW32$: $1.78 \times 10^6$ cpm/pmol $BW34$: $5.02 \times 10^6$ cpm/pmol Dentaturing gradient gel analysis comparison of the 3' radiolabeled probes to 5' kinased probes and BW35, show that the 3' radiolabeled probes ran in a similar fashion to the 5' radiolabeled probes.

Once again, the region amplified was the 350 base region on M13mp10w defined by primers BW36 and BW42. Primer sequences and locations are listed in Example I.

Each mixture consisted of adding $10^{-3}$ pmol of the target M13mp10w DNA to a 50 ul reaction volume containing 50 mM KCl, 10 mM Tris HCl pH 8.3, 3 mM MgCl$_2$, 10 pmol each of primers BW36 and BW42, 200 uM each of four deoxynucleoside triphosphates, 1.25 units of Tag DNA polymerase and either 2, 10, or 20 pmol of isotopically diluted probe DG46, BW32, or BW34.

A master reaction mix was made containing appropriate amounts of reaction buffer, nucleoside triphosphates, template and enzyme. Aliquots were made and to them was added the appropriate amount of primers and probes. Control reactions included all reaction components except primers, and all reaction components except probe.

Reaction mixtures were overlaid with 50 ul mineral oil, microcentrifuged and placed into a thermal cycler. Amplification scheme was as follows:

| | |
|---|---|
| Fifteen cycles: | 96° C. denaturation, 1 min |
| | 60° C. anneal/extension, 1.5 min |
| Final cycle: | 96° C. denaturation, 1 min |
| | 60° C. anneal/extension, 5.5 min |

After cycling, the mineral oil was extracted using 50 ul chloroform and samples were stored at 4° C.

Samples were analyzed by a 4% acrylamide gel, an 8% denaturing gradient acrylamide gel, and by homochromatography. For all three analyses, handling of reaction mixtures was as previously described.

In the 4% acrylamide gel analysis, a sharp band corresponding to the desired product at 350 bases was visible in all of the reaction mixtures except control reactions minus primers. In all of the reaction mixtures containing both primers and probe, a second band was visible at approximately 300 bases. This second band became more intense with increasing probe concentration, and probably corresponded to probe which was either not efficiently 3' radiolabeled or lost its 3' label, allowing probe extension to generate a second product.

An overnight exposure of the 8% denaturing gradient acrylamide gel showed a distribution of products ranging from full size probe down to less than 15 bases with all three probes being run. As would be expected, the 5'-3' nuclease activity of Tag DNA polymerase degraded the probe to a point where it was no longer stable and dissociated from the template.

The wide size distribution of products was illustrative of the continuously changing concentrations of reactants and temperature changes during PCR cycling. Such variations would lead to changes in annealing kinetics of probe and enzyme, allowing for probe to dissociate in a variety of sizes at different times in the cycling routine.

The homochromatography plate revealed the smallest product to be about 10 to 12 bases in length for all the probes examined. Since all three probes had identical sequence except at the 5' tail region, this result shows that for this particular probe sequence at an anneal/extend temperature of 60° C., the probe was degraded to about 10 bases and was then not stable enough to remain annealed to the template.

Example V: Polymerization Independent 5'-3' Nuclease Activity of Tag DNA Polymerase Tag DNA polymerase was able to liberate the 5' $^{32}$P-labeled end of a hybridized probe when positioned in the proximity of that probe by an upstream primer. A series of primers was designed to lie from zero to twenty bases upstream of hybridized kinased probe BW33.

BW37
    Delta-0 5' 5571-5542 3'
    5'-GCGCTAGGGCGCTGGCAAGTGTAGCGGTCA-3'

BW38
    Delta-1 5' 5572-5543 3'
    5'-GGCGCTAGGGCGCTGGCAAGTGTAGCGGTC-3'

BW39
    Delta-2 5' 5573-5544 3'
    5'-GGGCGCTAGGGCGCTGGCAAGTGTAGCGGT-3'

BW40
    Delta-5 5' 5576-5547 3'
    5'-AGCGGGCGCTAGGGCGCTGGCAAGTGTAGC-3'

BW41
    Delta-10 5' 5581-5552 3'
    5'-AAAGGAGCGGGCGCTAGGGCGCTGGCAAGT-3'

BW42
    Delta-20 5' 5591-5562 3'
    5'-GAAGAAAGCGAAAGGAGCGGGCGCTAGGGC-3'

About 0.5 pmol of probe BW33 and 0.5 pmol of one of each of the primers were annealed to 0.5 pmol M13mp10w in a 10.5 ul reaction volume containing 50 mM KCl, 10 mM Tris-HCl pH 8.3, and 3 mM MgCl$_2$. Control reaction mixtures contained either 20 uM or 200 uM each of four deoxynucleoside triphosphates. An additional primer, DG47, positioned 530 bases upstream from the probe was used.

DG47
    Delta-530 5' 6041-6012 3'
    5'-CGGCCAACGCGCGGGGAGAGGCGGTTTGCG-3'

Reaction mixtures were heated to 98° C. for 1 min and annealed at 60° C. for 30 min. Tubes were then microcentrifuged and placed in a water bath at 70° C. After ample time for reaction mixtures to equilibrate to temperature, 10, 5, 2.5, 1.25, or 0.3125 units of Taq DNA polymerase were added, and 4 ul aliquots were removed at 2, 5 and 10 min. Enzyme was inactivated by adding 4 ul 10 mM EDTA to each aliquot and placing at 4° C. Reaction mixtures were examined by homochromatography analysis.

Figure 4:
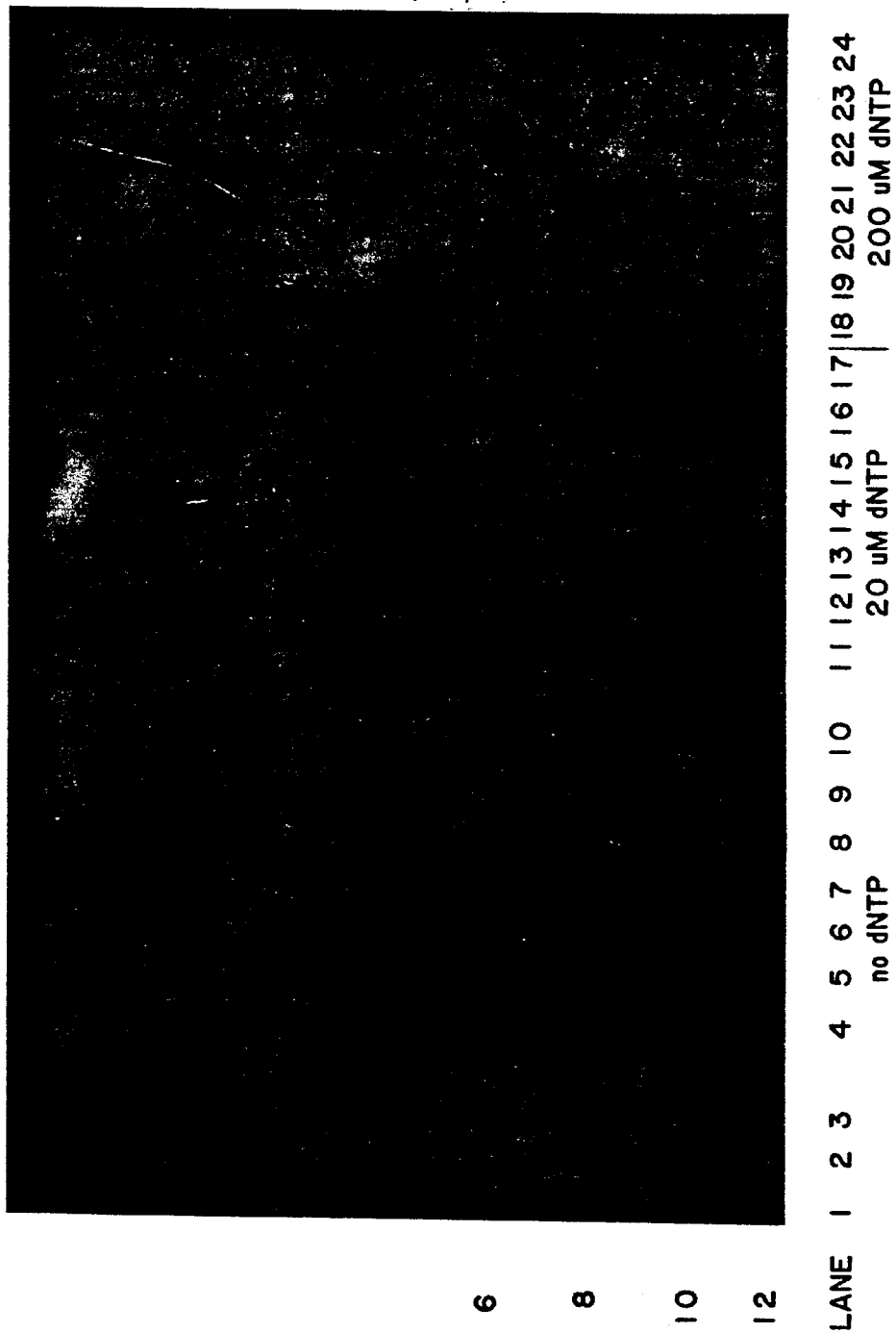
FIG. 4 illustrates the polymerization independent 5'-3' nuclease activity of Taq DNA polymerase shown in the autoradiograph using a series of primers which anneal from zero to 20 nucleotides upstream of the probe.

In the homochromatography analysis, 1 ul of each sample was spotted onto DEAE cellulose thin layer plates and placed into a development chamber containing Homo-Mix III at 70° C. Homo-Mix was allowed to migrate to the top of each plate, at which time the plates were removed, dried, covered with Saran Wrap, and autoradiographed. FIG. 4 shows the results of this experiment.

In FIG. 4, Lanes 1 through 3 contain radiolabeled oligonucleotide molecular size markers of 6, 8, 9, 10, 11, 12 and 13 nucleotides. Lanes 4-10 show reactions for primers BW37, BW38, BW39, BW40, BW41, BW42 and DG47, respectively, in the absence of dNTP's. Lanes 11-24 show control reactions for all primers in the presence of 20 mM or 200 mM dNTP.

In the absence of dNTPs, Taq DNA polymerase generated labeled probe fragments using all of the primers with considerably less label being released as the primer-probe spacing increased. This effect was seen at all the enzyme concentrations examined (0.3125 U to 10 U/reaction) and all timepoints. The sizes of fragments released were the same, about two and three bases in length, however, the primary species varied depending upon which primer was added. The majority species released by the delta zero and delta two primers was one base smaller than that released by the delta one, five, ten, and twenty primers. This nuclease activity was polymerization-independent and proximity-dependent.

In the presence of nucleoside triphosphates, the sizes of labeled probe fragments released, and the relative proportions of each, were identical for all the primers examined. Also, the sizes of products were larger by one to two bases when dNTPs were present. It may be that while the enzyme was polymerizing, it had a "running start" and as it encountered hybridized probe, was simultaneously displacing one to two bases and then cutting, thus generating a larger fragment.

There was no detectable difference in amount of product released when dNTPs were at 20 uM or 200 uM each and no significant differences were seen due to extension times or enzyme concentrations in the presence of dNTPs.

Example VI: Example to Illustrate the Nature of Released Product Based on Probe Sequence at the 5' End The effect of strong or weak base pairing at the 5' complimentary region of a probe on the size of released product was assessed. Two probes, BW50 and BW51, were designed to contain either a GC- or an AT-rich 5' complimentary region. BW50 and BW51 were compared to probe BW33 used in Example V.

BW50 =
    5' 5521-5496 3'
    5'-tatCCCGCCGCGCTTAATGCGCCGCTACA-3'

BW51 =
    5' 5511-5481 3'
    5'-gcaTTAATGCGCCGCTACAGGGCGCGTACTATGG-3'
    a, t, g, c = bases which are non-complementary to template strand BW50, BW51, and BW33 were labeled with $^{32}$P-ATP using polynucleotide kinase and had the following specific activities:

*BW*50: $1.70 \times 10^6$ cpm/pmol

*BW*51: $2.22 \times 10^6$ cpm/pmol

*BW*33: $1.44 \times 10^6$ cpm/pmol

The final concentration of all three probes was 0.10 pmol/ul.

Individually, 0.5 pmol of either probe BW50, BW51, or BW33 and 0.5 pmol of primer BW42 were annealed to 0.5 pmol of M13mp10w in a 10.5 ul reaction volume containing 50 mM KCl, 10 mM Tris HCl, pH 8.3, 3 mM MgCl$_2$ and 200 uM each of four deoxynucleoside triphosphates. Control samples contained all reaction components except template. For the annealing step, reaction mixtures were heated to 98° C. for 1 min and annealed at 60° C. for 30 min. Tubes were then microcentrifuged and placed in a water bath at 50° C., 60° C., or 70° C. After ample time for reaction mixtures to equilibrate to temperature, 0.3125 units of Taq DNA polymerase was added. Four ul aliquots were removed at 1, 2, and 5 min. Reactions were inactivated by adding 4 ul of 10 mM EDTA to each aliquot and placing at 4° C. Samples were examined by homochromatography analysis and the results are shown in FIGS. 5 and 6.

Figure 5:
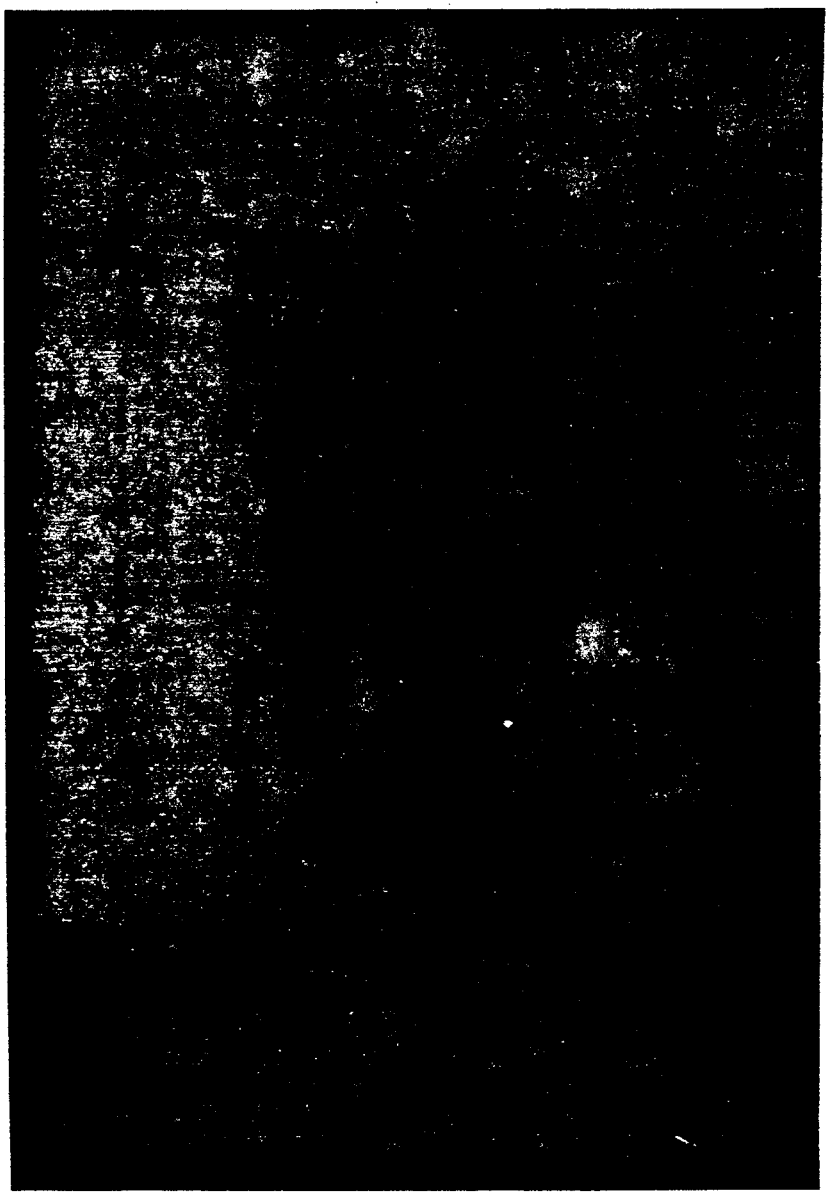
FIG. 5 is an autoradiograph showing the release of labeled probe fragments under increasing incubation temperatures and time, wherein the composition at the 5' end of the probe is GC rich.

FIG. 5 shows the reactions containing the 'GC'-rich probe BW50. Lanes 1-3 contain oligonucleotide molecular size markers of 6, 8, 9, 10, 11, 12, and 13 nucleotides. Lanes 4–6 show extension reactions performed at 50° C. for 1, 2, and 5 minutes. Lanes 7–9 show extension reactions at 60° C. for 1, 2, and 5 minutes. Lanes 10–12 show reactions at 70° C. for 1, 2, and 5 minutes. Lanes 13–15 are control reactions containing all components except template, incubated at 70° C. for 1, 2 and 5 minutes.

Figure 6:
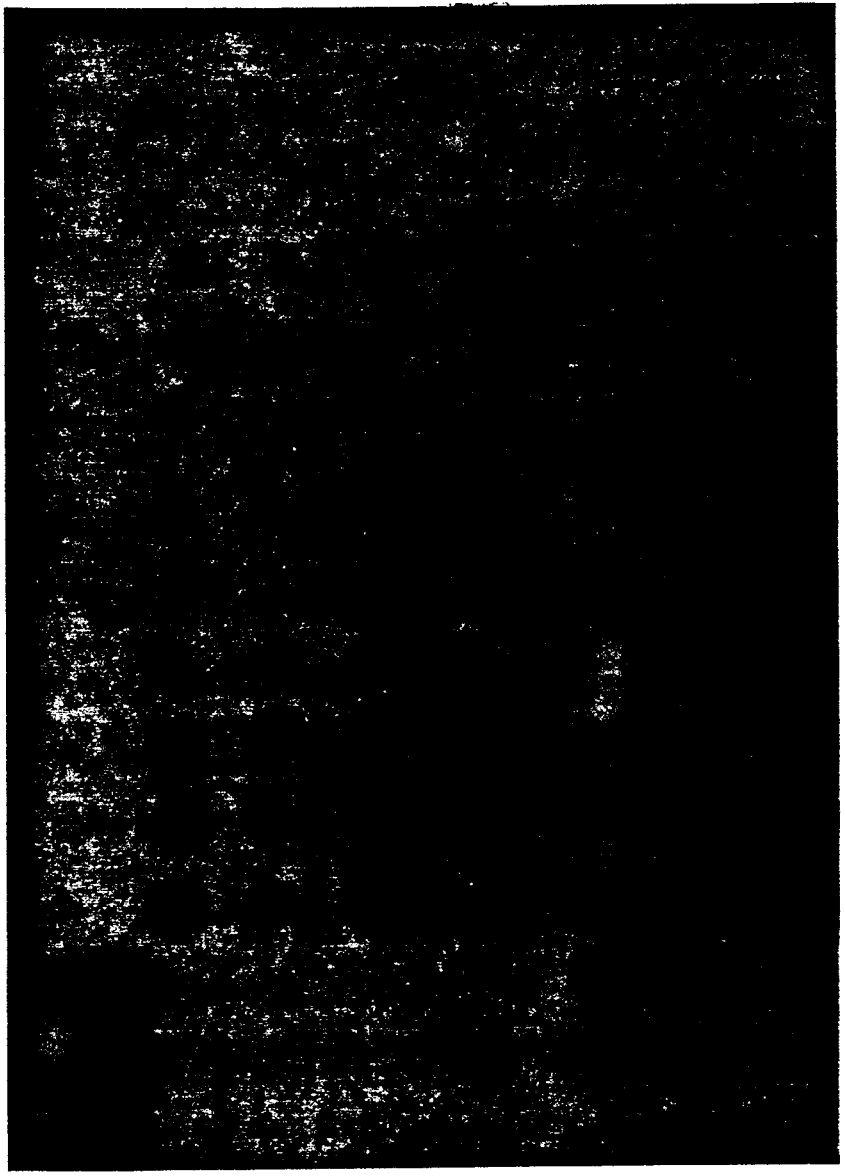
FIG. 6 is an autoradiograph showing the release of labeled probe fragments under increasing incubation temperatures and time, wherein the composition at the 5' end of the probe is AT rich.

FIG. 6 shows the reactions containing the 'AT' rich probe BW51. As in FIG. 5, Lanes 1–3 are oligonucleotide molecular size markers of 6, 8, 9, 10, 11, 12 and 13 nucleotides. Lanes 4–6 are extension reactions performed at 50° C. for 1, 2 and 5 minutes. Lanes 7–9 are reactions at 60° C. at 1, 2, and 5 minutes. Lanes 10–12 are reactions at 70° C. at 1, 2, and 5 minutes. Lanes 13–15 are control reactions containing all components except template, incubated at 70° C. for 1, 2 and 5 minutes.

The results demonstrate that the nature of probe label release was dependent on temperature and base composition at the 5' end. The more stable GC-rich probe BW50 showed little label release at 50° C. (FIG. 5, Lanes 4–6) and increasingly more at 60° FIG. 5, Lanes 7–9) and 70° C. (FIG. 5, Lanes 10–12 . The major products released were about 3–5 bases in length. BW51, which was AT-rich at the 5' end, showed as much label release at 50° C. (FIG. 6, Lanes 4–6) as was observed at the higher temperatures. In addition, the AT-rich probe generated larger-sized products than the GC-rich probe. Its base composition may give the opportunity for a greater "breathing" capacity, and thus allow for more probe displacement before cutting, and at lower temperatures than the GC-rich probe.

Example VII: HIV Capture Assay

The following is an example of the use of a dual labeled probe containing biotin in a PCR to detect the presence of a target sequence. Two oligonucleotides, BW73 and BW74, each complimentary to a portion of the HIV genome, were synthesized with a biotin molecule attached at their 3' ends. The 5' end of each oligonucleotide was additionally labeled with $^{32}P$ using polynucleotide kinase and $^{32}P$-ATP. The two oligonucleotides PH7 and PH8 are also complimentary to the HIV genome, flank the region containing homology to the two probe oligonucleotides and can serve as PCR primers defining a 142 base product.

BW73 = $^{32}P$-GAGACCATCAATGAGGAAGCTGCAGAATGGGAT-Y

BW74 = $^{32}P$-gtgGAGACCATCAATGAGGAAGCTGCAGAATGGGAT-Y

PH7 = AGTGGGGGGACATCAAGCAGCCATGCAAAT

PH8 = TGCTATGTCAGTTCCCCTTGGTTCTCT

Y = biotin
lower case indicates bases which are non-complementary to template strand A set of 50 ul polymerase chain reactions was constructed containing either BW73 or BW74, each doubly labeled, as probe oligonucleotides at 2 nM. Additionally, HIV template in the form of a plasmid clone was added at either $10^2$ or $10^3$ copies per reaction, and primer oligonucleotides PH7 and PH8 were added at 0.4 uM each. Taq polymerase was added at 1.25 U per reaction and dNTPs at 200 uM each. Each reaction was overlayed with 50 ul of oil, spun briefly in a microcentrifuge to collect all liquids to the bottom of the tube, and thermocycled between 95° C. and 60° C., pausing for 60 sec at each temperature, for 30, 35 or 40 cycles.

At the conclusion of the thermocycling, each reaction was extracted with 50 ul of $CHCl_3$ and the aqueous phase collected.

Each reaction was analyzed for amplification by loading 3 ul onto a 5% acrylamide electrophoresis gel and examined for the expected 142 base pair product. Additionally, 1 ul of each reaction was examined by TLC homochromotography on DEAE cellulose plates. Finally, each reaction was further analyzed by contacting the remaining volume with 25 ul of a 10 mg/ml suspension of DYNABEADS M-280 streptavidin labeled, superparamagnetic, polystyrene beads. After reacting with the beads, the mixture was separated by filtration through a Costar Spin X centrifuge filter, the filtrate collected and the presence of released radiolabeled determined.

Figure 7A:
FIG. 7A and 7B provides 5% acrylamide electrophoresis gel analysis of a 142 base pair HIV product, amplified in the presence or absence of labeled probe.
Figure 7B:
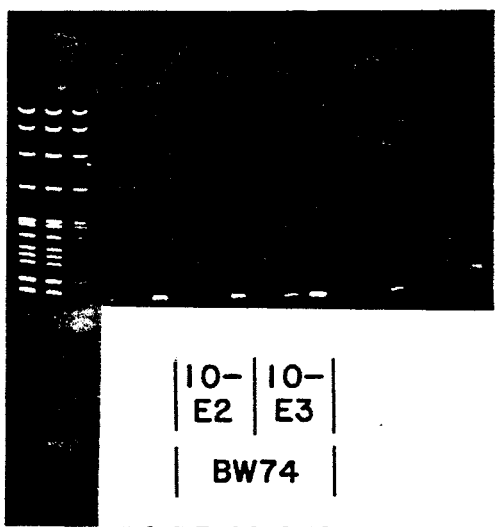

FIG. 7 contains images of the two gels used and shows that 142 base pair product occurs in all reactions, with and without probe, and FIG. 7 increases in amount both as starting template was increased from $10^2$ to $10^3$ copies and as thermocycling was continued from 30 to 35 and 40 cycles.

Figure 8A:
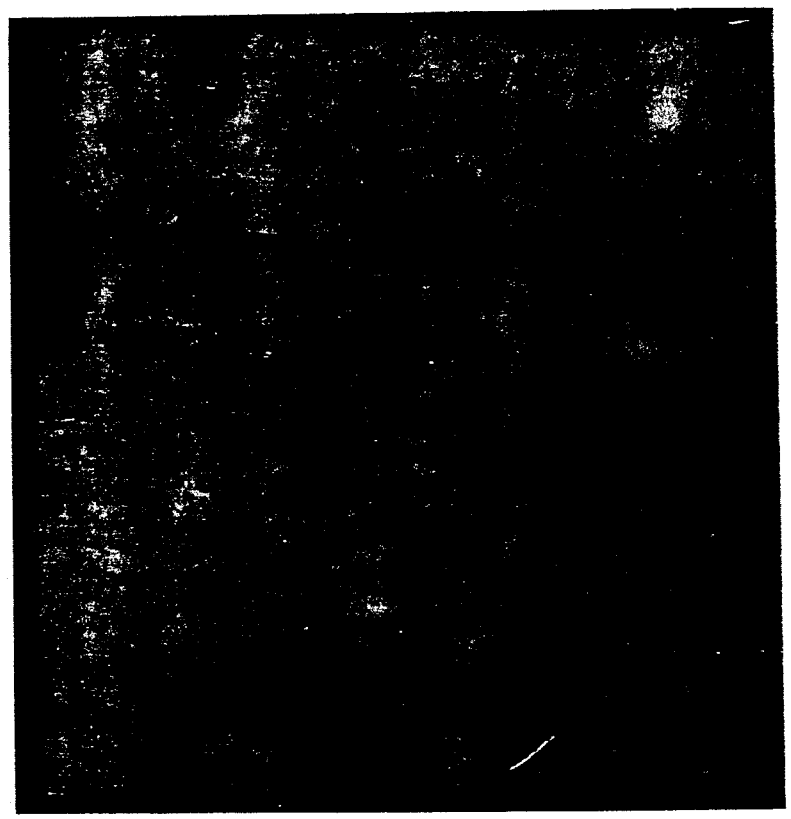
FIG. 8A and 8B are autoradiographs of TLC analysis of aliquots of PCR amplification products which show that radiolabel release occurs and increases in amount with both increases in starting template and with longer thermocycling.
Figure 8B:

FIG. 8 is a composite of two autoradiographs of the TLC analysis of aliquots of the PCRs and show that radiolabel release occurs and increases in amount with both increases in starting template and with longer thermocycling. In the first TLC of PCRs using BW73, lanes 1 and 3 contain radiolabeled oligonucleotides 2 and 3 bases in length as size standards. Lanes 4, 5 and 6 contain samples from PCRs with $10^2$ starting copies of template and lanes 7, 8 and 9 with $10^3$ starting copies. Samples in lanes 4 and 7 were thermocycled for 30 cycles, in lanes 5 and 8 for 35 cycles and in lanes 6 and 9 for 40 cycles. In the second TLC of PCRs using BW74, lanes 1 and 2 are the radiolabeled 2 mer and 3 mer, lanes 4, 5 and 6 contain samples from PCRs with $10^2$ starting copies of template thermocycled for 30, 35 and 40 cycles, respectively, and lanes 7, 8 and 9 with $10^3$ copies of starting template thermocycled for 30, 35 and 40 cycles, respectively. The size of the released label is smaller with BW73 having no 5' non-complimentary bases as expected and larger with BW74 which has a 5' three base non-complimentary extension.

Each chromatogram was additionally analyzed by two dimensional radioisotope imaging using an Ambis counter. The results of Ambis counting and bead capture counting shown in Table 1. The good agreement in the two methods of measuring label release demonstrates the practicality of the use of labeled biotinylated probes and avidinylated beads in PCRs to determine product formation.

TABLE 1

| | Number of Cycles | % of Label Released | |
|---|---|---|---|
| | | Ambis | Capture |
| BW73 | | | |
| $10^2$ copies | 30 | 6.9 | 10.8 |

TABLE 1-continued

| | Number of Cycles | % of Label Released | |
|---|---|---|---|
| | | Ambis | Capture |
| | 35 | 29.0 | 32.7 |
| | 40 | 47.2 | 47.2 |
| $10^3$ copies | 30 | 11.8 | 16.8 |
| | 35 | 35.6 | 39.3 |
| | 40 | 53.4 | 52.5 |
| BW74 | | | |
| $10^2$ copies | 30 | 8.3 | 7.9 |
| | 35 | 20.7 | 25.2 |
| | 40 | 43.2 | 48.3 |
| $10^3$ copies | 30 | 15.7 | 14.7 |
| | 35 | 32 | 37.7 |
| | 40 | 46 | 47.9 |

Although the foregoing invention has been described in some detail for the purpose of illustration, it will be obvious that changes and modifications may be practiced within the scope of the appended claims by those of ordinary skill in the art.

We claim:

1. A process for the detection of a target nucleic acid sequence in a sample, said process comprising:
   (a) contacting a sample comprising single-stranded nucleic acids with an oligonucleotide containing a sequence complementary to a region of the target nucleic acid and a labeled oligonucleotide containing a sequence complementary to a second region of the same target nucleic acid sequence strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3' end of the first oligonucleotide is upstream of the 5' end of the labeled oligonucleotide;
   (b) maintaining the mixture of step (a) with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments; and
   (c) detecting and/or measuring the release of labeled fragments.

2. The process of claim 1 wherein the 3' end of the first oligonucleotide in the annealed duplex of step (a) is within about 20 nucleotides of the 5' end of an annealed, labeled oligonucleotide, thereby having spacing effective to permit the release of labeled fragments in the absence of nucleic acid polymerization.

3. The process of claim 1 wherein the oligonucleotides comprise deoxyribonucleotides.

4. The process of claim 1 wherein the nucleic acid polymerase is a DNA polymerase having a 5' to 3' nuclease activity.

5. The process of claim 1 wherein a nucleotide within the label oligonucleotide is modified to control nuclease cleavage specificity.

6. The process of claim 1 wherein said labeled oligonucleotide comprises at least one label.

7. The process of claim 1 wherein the labeled oligonucleotide comprises first and second labels wherein the first label is separated from the second label by a nuclease susceptible cleavage site.

8. The process of claim 6 wherein the labeled oligonucleotide is labeled at the 5' terminus.

9. The process of claim 7 wherein the labeled oligonucleotide further comprises a tail of non-nucleic acids or a sequence of nucleotides which is non-complementary to the target nucleic acid sequence.

10. The process of claim 9 wherein the label is attached to a nucleotide in the tail or non-complementary sequence.

11. The process of claim 10 wherein the label is at the 5' terminus and is separated from the sequence complementary to the target nucleic acid sequence by the tail or non complementary sequence.

12. The process of claim 1 performed under conditions sufficient to promote nucleic acid polymerization, wherein the release of labeled fragments occurs during extension of the first oligonucleotide.

13. A polymerase chain reaction (PCR) amplification process for detecting a target nucleic acid sequence in a sample, said process comprising:
   (a) providing to a PCR assay containing said sample, at least one labeled oligonucleotide containing a sequence complementary to a region of the target nucleic acid, wherein said labeled oligonucleotide anneals within the target nucleic acid sequence bounded by the oligonucleotide primers of step (b);
   (b) providing a set of oligonucleotide primers, wherein a first primer contains a sequence complementary to a region in one strand of the target nucleic acid sequence and primes the synthesis of a complementary DNA strand, and a second primer contains a sequence complementary to a region in a second strand of the target nucleic acid sequence and primes the synthesis of a complementary DNA strand; and wherein each oligonucleotide primer is selected to anneal to its complementary template upstream of any labeled oligonucleotide annealed to the same nucleic acid strand;
   (c) amplifying the target nucleic acid sequence employing a nucleic acid polymerase having 5' to 3' nuclease activity as a template-dependent polymerizing agent under conditions which are permissive for PCR cycling steps of (i) annealing of primers and labeled oligonucleotide to a template nucleic acid sequence contained within the target sequence, and (ii) extending the primer wherein said nucleic acid polymerase synthesizes a primer extension product while the 5' to 3' nuclease activity of the nucleic acid polymerase simultaneously releases labeled fragments from the annealed duplexes comprising labeled oligonucleotide and its complementary template nucleic acid sequences, thereby creating detectable labeled fragments; and
   (d) detecting and/or measuring the release of labeled fragments to determine the presence or absence of the target sequence in the sample.

14. The PCR process of claim 13 wherein said nucleic acid polymerase is a thermostable enzyme.

15. The PCR process of claim 14 wherein said thermostable enzyme is the DNA polymerase from a Thermus species.

16. The PCR process of claim 13 wherein the 3' end of an annealed oligonucleotide primer is within about 20 nucleotides the 5' end of the labeled oligonucleotide annealed to the same nucleic acid strand.

17. The PCR process of claim 16 wherein said labeled oligonucleotide has a blocked 3' terminus to prevent extension by the nucleic acid polymerase.

18. The PCR process of claim 16 wherein the labeled oligonucleotide further comprises a sequence of one to about ten nucleotides which sequence is substantially non-complementary to the target nucleic acid sequence.

19. The PCR process of claim 13 wherein the labeled oligonucleotide comprises first and second labels wherein the first label is separated from the second label by a nuclease susceptible cleavage site.

20. The PCR process of claim 13 wherein a pair of labeled oligonucleotides probes are provided in step (a).

21. The PCR process of claim 20 wherein said pair of labeled probes anneal to different, non-overlapping regions of the same complementary nucleic acid strand, wherein the 5' end of the second labeled probe is adjacent the 3' end of the first labeled probe.

22. The PCR process of claim 18 wherein the label is attached to a nucleotide in the non complementary sequence.

23. The PCR process of claim 22 wherein the label is at the 5' terminus and is separated from the complementary probe sequence by the non-complementary sequence.

24. The PCR process of claim 13 wherein the oligonucleotide is labeled at the 5' terminus.

25. The PCR process of claim 17 wherein the oligonucleotide is labeled at the blocked 3' terminus.

26. The PCR process of claim 13 wherein the label is attached to an internal sequence of the oligonucleotide.

27. The PCR process of claim 13 wherein the label provides a signal proportional to the number of target nucleic acid sequences amplified.

28. The PCR process of claim 13 wherein the label is a deoxyribonucleoside analog having signal-generating properties.

29. The PCR process of claim 13 wherein the labeled oligonucleotide comprises a pair of interactive signal-generating labels effectively positioned on the oligonucleotide to quench the generation of detectable signal, said labels being separated by a site within the oligonucleotide susceptible to nuclease cleavage, thereby allowing, during primer extension, the 5' to 3' nuclease activity of the nucleic acid polymerase to separate the first interactive signal generating label from the second interactive signal generating label by cleaving at the susceptible site thereby yielding a detectable signal.

30. The PCR process of claim 29 wherein said first label is a chemiluminescent substrate and said second label is a fluorophore which interacts therewith.

31. The PCR process of claim 13 wherein the label of said oligonucleotide is attached through a spacer arm of sufficient length to permit the 5' to 3' nuclease activity of the nucleic acid polymerase to release labeled fragments.

32. The PCR process of claim 13 wherein the melting temperature ($T_m$) differential between the labeled oligonucleotide and its' associated upstream oligonucleotide primer is effective to provide preferential binding of the labeled oligonucleotide during the annealing step of PCR cycles.

33. The PCR process of claim 32 wherein the $T_m$ of the labeled oligonucleotide is as great as 40° C. higher than the $T_m$ of the upstream oligonucleotide primer.

34. The PCR process of claim 13 wherein the labeled oligonucleotide fragments comprise a mixture of mono-, di and larger nucleotide fragments.

35. The PCR process of claim 13 which further comprises separating labeled oligonucleotide fragments from other components in the PCR mixture prior to detection of labeled fragments.

36. The PCR process of claim 35 wherein the separation step uses size exclusion chromatography.

37. The PCR process of claim 35 wherein the labeled fragments are separated from the PCR mixture by solid phase extraction.

38. The PCR process of 37 wherein avidin or streptavidin is attached to the solid phase and the labeled oligonucleotide further comprises a bound biotin molecule separated from the label by a nuclease susceptible cleavage site.

* * * * *

UNITED STATES PATENT AND TRADEMARK OFFICE
CERTIFICATE OF CORRECTION

PATENT NO. : 5,210,015

DATED : May 11, 1993

INVENTOR(S) : David H. Gelfand, Pamela M. Holland, Randall K. Saiki, and Robert M. Watson It is certified that error appears in the above-identified patent and that said Letters Patent is hereby corrected as shown below:

Column 3, line 38, please delete "Tag" and insert therefor --Taq--.

Column 4, line 37, please delete "=" and insert therefor --'--.

Column 6, line 14, please delete "Tag" and insert therefor --Taq--.

Column 6, line 18, please delete "Tag" and insert therefor --Taq--.

Column 6, line 20, please delete "Tag" and insert therefor --Taq--.

Column 8, line 39, please delete "Non complementary" and insert therefor --Non-complementary--.

Column 8, lines 43 and 44, please delete "non complementary" and insert therefor --non-complementary--.

Column 8, lines 48 and 49, after "encounters" please insert --this duplex--.

Column 11, line 46, please delete "(Tag)" and insert therefor --(Taq)--.

Column 14, line 10, please delete "Tag" and insert therefor --Taq--.

Column 14, line 29, please delete "Tag" and insert therefor --Taq--.

Column 14, line 35, please delete "Tag" and insert therefor --Taq--.

Column 16, line 42, please delete "Tag" and insert therefor --Taq--.

Column 16, line 47, please delete "Tag" and insert therefor --Taq--.

Column 17, line 51, please delete "Tag" and insert therefor --Taq--.

Column 18, line 52, after "through" please delete "1" and insert therefor --11--.

Column 19, line 61, please delete "Tag" and insert therefor --Taq--.

Column 20, line 42, please delete "Tag" and insert therefor --Taq--.

UNITED STATES PATENT AND TRADEMARK OFFICE
CERTIFICATE OF CORRECTION

PATENT NO. : 5,210,015

DATED : May 11, 1993

INVENTOR(S) : David H. Gelfand, Pamela M. Holland, Randall K. Saiki, and Robert M. Watson It is certified that error appears in the above-identified patent and that said Letters Patent is hereby corrected as shown below:

Column 20, line 62, please delete "Tag" and insert therefor --Taq--.
Column 20, line 63, please delete "Tag" and insert therefor --Taq--.
Column 21, line 38, please delete "Tag" and insert therefor --Taq--.
Column 21, line 59, please delete "Tag" and insert therefor --Taq--.
Column 22, line 61, please delete "Tag" and insert therefor --Taq--.
Column 23, line 63, please delete "Tag" and insert therefor --Taq--.

Column 24, line 31, please delete "103" and insert therefor --$10^3$--.
Column 27, Claim 22, line 2, please delete "non complementary" and insert therefor --non-complementary--.

Signed and Sealed this

Nineteenth Day of July, 1994

BRUCE LEHMAN

*Attest:*

*Attesting Officer*   *Commissioner of Patents and Trademarks*